(12) United States Patent
Sung et al.

(10) Patent No.: US 6,423,509 B1
(45) Date of Patent: Jul. 23, 2002

(54) *PICHIA PASTORIS* STRAIN FOR PRODUCING LACTOFERRIN AND METHODS OF USE

(75) Inventors: Chang Keun Sung; In Sun Joo; Moon Sook Woo; Sang Kyu Kim; Jeong Hyun Lee, all of Taejon; Keum Soon Lee, Choongchungbook-Do; Seung Suh Hong, Taejon; Hyun-Soo Lee, Seoul; Young Ho Kim, Taejon, all of (KR)

(73) Assignee: Samyang Genex Corporation, Seaoul (KR)

( * ) Notice: Subject to any disclaimer, the term of this patent is extended or adjusted under 35 U.S.C. 154(b) by 0 days.

(21) Appl. No.: 09/508,734
(22) PCT Filed: Jul. 14, 1999
(86) PCT No.: PCT/KR98/00373
§ 371 (c)(1),
(2), (4) Date: Jun. 1, 2000
(87) PCT Pub. No.: WO00/04132
PCT Pub. Date: Jan. 27, 2000

(30) Foreign Application Priority Data

Jul. 15, 1998 (KR) .............................. 98/29351

(51) Int. Cl.[7] ................................................ C12P 21/06
(52) U.S. Cl. ................... 435/69.1; 435/254.23; 435/254.1
(58) Field of Search ......................... 435/255.5, 254.23, 435/69.1

(56) References Cited

FOREIGN PATENT DOCUMENTS

| WO | WO 91/13982 | 9/1991 |
|---|---|---|
| WO | WO 93/22348 | 11/1993 |

OTHER PUBLICATIONS

Yim et al., J. Korean Soc. Food Sci. Nutr. 26(4), 669–674 (1997), in Korean.
Liang et al., I. Agric. Food Chem. 41(10), 1800–7 (1993).

*Primary Examiner*—Ponnathapu Achutamurthy
*Assistant Examiner*—Kathleen Kerr
(74) *Attorney, Agent, or Firm*—Darby & Darby

(57) ABSTRACT

The present invention relates to a method of mass-producing lactoferrin polypeptides from yeast which is resistant to lactoferrin polypeptides. The present invention also provides Pichia strains, especially *Pichia pastoris* KCTC 0500BP, that are resistant to lactoferrin polypeptides.

2 Claims, 6 Drawing Sheets

SEQUENCE LISTING

<160> NUMBER OF SEQ ID NOS: 12

<210> SEQ ID NO 1

-continued

```
<211> LENGTH: 35
<212> TYPE: DNA
<213> ORGANISM: Artificial Sequence
<220> FEATURE:
<223> OTHER INFORMATION: primer

<400> SEQUENCE: 1
ggaagcttaa aagatacgta aaatgcttcc aatgg                               35

<210> SEQ ID NO 2
<211> LENGTH: 30
<212> TYPE: DNA
<213> ORGANISM: Artificial Sequence
<220> FEATURE:
<223> OTHER INFORMATION: primer

<400> SEQUENCE: 2
gggaattctc aaaatctctt tatgcagctg                                     30

<210> SEQ ID NO 3
<211> LENGTH: 66
<212> TYPE: DNA
<213> ORGANISM: Homo sapiens
<220> FEATURE:
<221> NAME/KEY: CDS
<222> LOCATION: (1)..(66)

<400> SEQUENCE: 3 aaa tgc ttc caa tgg caa agg aat atg aga aaa gtg cgt ggc cct cct    48
Lys Cys Phe Gln Trp Gln Arg Asn Met Arg Lys Val Arg Gly Pro Pro
 1               5                  10                  15 gtc agc tgc ata aag aga                                              66
Val Ser Cys Ile Lys Arg
            20

<210> SEQ ID NO 4
<211> LENGTH: 22
<212> TYPE: PRT
<213> ORGANISM: Homo sapiens

<400> SEQUENCE: 4

Lys Cys Phe Gln Trp Gln Arg Asn Met Arg Lys Val Arg Gly Pro Pro
 1               5                  10                  15

Val Ser Cys Ile Lys Arg
            20

<210> SEQ ID NO 5
<211> LENGTH: 72
<212> TYPE: DNA
<213> ORGANISM: Homo sapiens
<220> FEATURE:
<221> NAME/KEY: CDS
<222> LOCATION: (1)..(72)

<400> SEQUENCE: 5 gta aaa tgc ttc caa tgg caa agg aat atg aga aaa gtg cgt cct cct    48
Val Lys Cys Phe Gln Trp Gln Arg Asn Met Arg Lys Val Arg Pro Pro
 1               5                  10                  15 cct gtc agc tgc ata aag aga ttt                                      72
Pro Val Ser Cys Ile Lys Arg Phe
            20

<210> SEQ ID NO 6
<211> LENGTH: 24
<212> TYPE: PRT
<213> ORGANISM: Homo sapiens
```

<400> SEQUENCE: 6

Val Lys Cys Phe Gln Trp Gln Arg Asn Met Arg Lys Val Arg Pro Pro
  1               5                  10                  15

Pro Val Ser Cys Ile Lys Arg Phe
             20

<210> SEQ ID NO 7
<211> LENGTH: 87
<212> TYPE: DNA
<213> ORGANISM: Homo sapiens
<220> FEATURE:
<221> NAME/KEY: CDS
<222> LOCATION: (1)..(87)

<400> SEQUENCE: 7 gag gct gaa gct tac gta aaa tgc ttc caa tgg caa agg aat atg aga       48
Glu Ala Glu Ala Tyr Val Lys Cys Phe Gln Trp Gln Arg Asn Met Arg
  1               5                  10                  15 aaa gtg cgt ggc cct cct gtc agc tgc ata aag aga ttt                   87
Lys Val Arg Gly Pro Pro Val Ser Cys Ile Lys Arg Phe
             20                  25

<210> SEQ ID NO 8
<211> LENGTH: 29
<212> TYPE: PRT
<213> ORGANISM: Homo sapiens

<400> SEQUENCE: 8

Glu Ala Glu Ala Tyr Val Lys Cys Phe Gln Trp Gln Arg Asn Met Arg
  1               5                  10                  15

Lys Val Arg Gly Pro Pro Val Ser Cys Ile Lys Arg Phe
             20                  25

<210> SEQ ID NO 9
<211> LENGTH: 26
<212> TYPE: DNA
<213> ORGANISM: Artificial Sequence
<220> FEATURE:
<223> OTHER INFORMATION: primer

<400> SEQUENCE: 9
ggctcgagct tggactgtgt ctggct                                          26

<210> SEQ ID NO 10
<211> LENGTH: 29
<212> TYPE: DNA
<213> ORGANISM: Artificial Sequence
<220> FEATURE:
<223> OTHER INFORMATION: primer

<400> SEQUENCE: 10
ggctcgagtt aatcmagggt cacagcatc                                       29

<210> SEQ ID NO 11
<211> LENGTH: 201
<212> TYPE: DNA
<213> ORGANISM: cow

<400> SEQUENCE: 11
cttggactgt gtctggctgc cccgaggaaa aacgttcgat ggtgtaccat ctcccaaccc     60
gagtggttca aatgccgccg atggcagtgg aggatgaaga agctgggtgc tccctctatc    120
acctgtgtga ggagggcctt tgccttggaa tgtatccggg ccatcgcgga gaaaaggcg     180

-continued

```
gatgctgtga ccctggatgg t                                              201

<210> SEQ ID NO 12
<211> LENGTH: 201
<212> TYPE: DNA
<213> ORGANISM: Korean cow

<400> SEQUENCE: 12
cttggactgt gtctggctgc cccgaggaaa aacgttcgat ggtgtaccat ctcccgaccc     60
gagtggttca aatgccgccg atggcagtgg aggatgaaga agctgggtgc tccctctatc   120
acctgtgtga ggagggcctt tgccttggaa tgtatccggg ccatcgcgga gaaaaaggcg   180
gatgctgtga cccttgatta a                                             201
```

PICHIA PASTORIS STRAIN FOR PRODUCING LACTOFERRIN AND METHODS OF USE

TECHNICAL FIELD AND BACKGROUND ART

Lactoferrin is a glycoprotein that has physiological and biological characteristics such as bactericidal, growth stimulatory, iron carrying activity, immune modulation, and specific reaction to membrane receptors.

The structure of human lactoferrin is composed of 681 amino acid residues. There is an iron-binding site in between the domains of one of the two lobes. Lactoferrin is known to have immuno-stimulatory effect and antibacterial activity. Also, it is reported that the peptides or polypeptides derived from lactoferrin are superior to lactoferrin itself in antibacterial activity and stability (U.S. Pat. No. 5,304,633; 5,571,697). Therefore, lactoferrin polypeptide is a good additive for infant formulas and animal feed or drugs due to its bacteriostatic, cell growth stimulatory or inflammation inhibitory effects.

Lactoferrin polypeptides have been isolated mainly from milk serum. Recently, mass production of polypeptides by genetic engineering have been attempted. Ward and Piddington have produced 2 g/l quantity of recombinant lactoferrin in *Aspergillus oryzae* using a glucoamylase promoter (Ward, P. P. et.al., *Biotechnology*, 13:498–503 (1995)). Qianwa reported that 1.5~2.0 mg/l of recombinant human lactoferrin was obtained by expressing it in the form of a fusion protein between a yeast invertase and human lactoferrin by using a chelatin promoter in *Saccharomyces cerevisiae* (Qianwa Liang et.al., *J. Agric. Food. Chem.* 41:1800–1907 (1989)). It was discussed that the recombinant lactoferrin synthesized from *S. cerevisiae* had additional sugar units, and the yield was not reproducible. In the case of producing lactoferrin or its antibacterial peptide derivatives by using genetic engineering techniques, expressed lactoferrin or antibacterial peptide could slow down the growth of or even kill the host microorganism. To overcome this problem, it is reported that the antibacterial peptide was expressed in the form of a fusion peptide. In U.S. Pat. No. 5,571,697, antibacterial polypeptide derived from lactoferrin was expressed as a fusion protein in Aspergillus.

BRIEF SUMMARY OF THE INVENTION

The present invention provides a method to mass-produce lactoferrin polypeptide from microorganisms.

The present invention provides a method to mass-produce lactoferrin polypeptide alone from microorganisms.

The present invention provides a novel germ strain, which is resistant against lactoferrin polypeptide.

The present invention provides a germ strain that produces lactoferrin polypeptide.

DETAILED DESCRIPTION OF THE INVENTION

Figure 1:
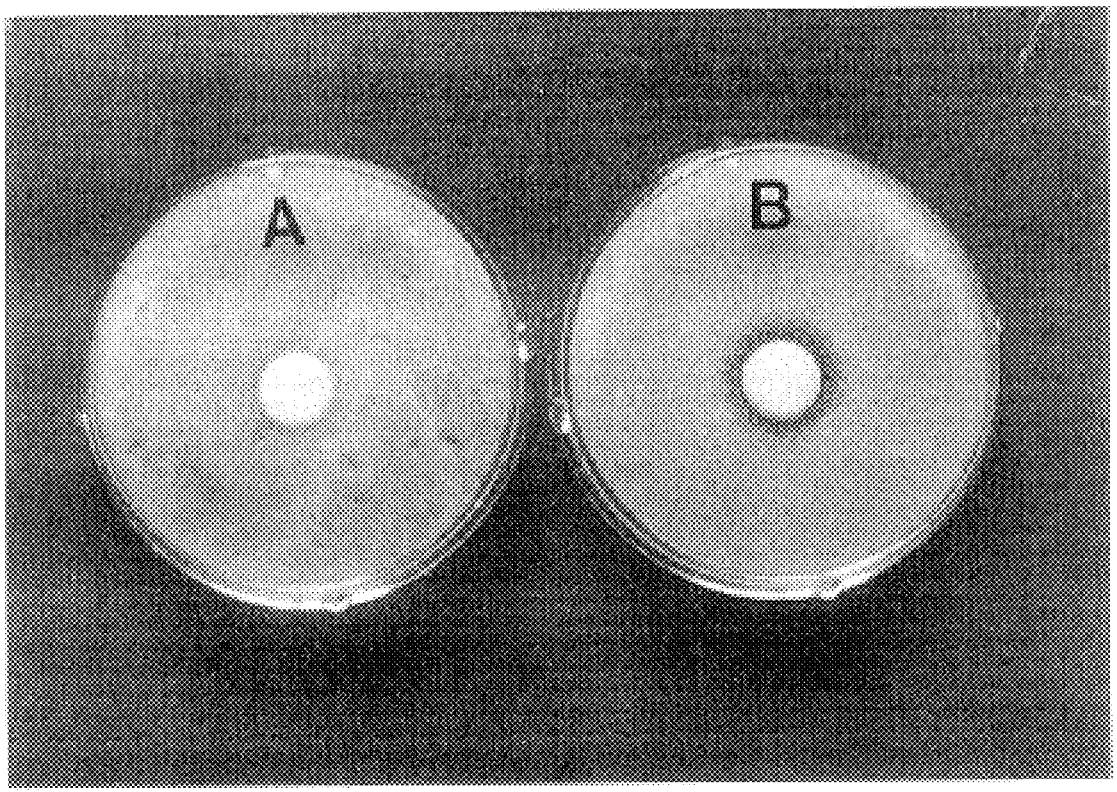
FIG. 1 is a photograph showing the resistance of microorganisms against lactoferrin polypeptide of the present invention.

The present inventors have explored lactoferrin polypeptide resistant germ strains from samples of soybean sauce, soybean paste and wine obtained from Choongchung province, Korea. The inventors also screened and identified superior lactoferrin polypeptide resistant strains.

In the present application lactoferrin polypeptides means lactoferrin or all of the antibacterial peptides or polypeptides derived from lactoferrin unless otherwise specified. The origin of the lactoferrin is not limited, and the lactoferrin can be from human, cow, pig or other mammals.

Since the microorganism of the present invention is extremely resistant against lactoferrin polypeptide, the lactoferrin polypeptide can be produced as a fusion protein or a peptide itself by the microorganism of the present invention.

Also the microorganism of the present invention can be used in mass-producing not only lactoferrin polypeptide but also other antibacterial peptides that are difficult to mass-produce due to its activity to slow down the growth of or to kill the host cells.

The present invention also relates to the method of mass-producing the lactoferrin polypeptides from microorganisms composed of the following steps:

preparing a plasmid vector composed of a promoter sequence active in a yeast cell and a sequence that is connected to the promoter and which codes the lactoferrin polypeptide;

transforming the lactoferrin polypeptide resistant yeast with the above vector; and culturing the transformed yeast.

The yeast cell of the present invention can be selected from Saccharomyces, Aspergillus, Pichia, and Candida, and preferably Pichia genus cells.

In the preparation method of the present invention, the sequence coding lactoferrin polypeptide can be a sequence coding a fusion polypeptide fused with another peptide or a sequence coding additional amino acid residues in addition to the lactoferrin polypeptide or a sequence coding the lactoferrin polypeptide only. An altered sequence can also be used if it codes the identical polypeptide as the lactoferrin polypeptides.

The present invention is also directed to the *Pichia pastoris* cell that contains the vector having the lactoferrin polypeptide genes.

The restriction enzymes and other enzymes used in the Examples of the present invention were obtained from Boehringer Mannheim Biochemical Company. Oligonucleotide primer was obtained from Invitrogen, and the components of the media such as amino acids, yeast nitrogen base (YNB), yeast extracts, peptone and glucose were obtained from Difco. Human lactoferrin and other reagents used in the protein electrophoresis were obtained from Sigma.

*E. coli* Top10F' and *Pichia pastoris* SJW-28 of the present invention were used in the transformation.

The compositions of the media in the present invention are as follows.

YM medium: yeast extracts 0.3%, malt extract 0.3%, peptone 0.5%, dextrose 1%, agar 2%.

YM-L medium: the medium that contains 1 mg of lactoferrin-pepsin hydrolysis product in 1 ml YM medium.

YPD liquid medium: yeast extract 1%, peptone 2%, dextrose 2%.

The invention will be further illustrated by the following examples, but the invention is not limited to the examples given.

EXAMPLE 1

Selection of the Host Microorganism that is Resistant Against Lactoferrin Polypeptide The lactoferrin polypeptide resistant microorganisms were selected primarily by smearing wine and soybean sauce samples in YM-L medium.

Secondary verification of the antibacterial activity against lactoferrin polypeptide was performed by following the method by H. Wakabayashi (Hiroyuki Wakabayashi, et.al., J. Food Protection, 55(4):280–240.6 (1992)). In a medium containing the primarily selected germs, a paper disk that was immersed in the lactoferrin hydrolysis product that was obtained by treating 1 ml of lactoferrin 1 mg/citrate buffer solution at pH 2 with pepsin (10 unit/ml) at 37° C. for 4 hours was placed. A formation of a clear zone was observed. The germ strains that had excellent resistance against lactoferrin polypeptide were selected (FIG. 1) and named as "SJW-28". The identification procedure using a PI-CHE kit and other microorganism identification methods, based on N. J. W. Kreger-Van Rij. 1987 were used. The yeasts: a taxonomic study third revised and enlarged edition, Elsevier, were used to identify it as *P. pastoris* or related germ strains. This cell line was deposited at the Korean Collection of Type Cultures (KCTC) in Korea Research Institute of Bioscience and Biotechnology located at Yusung-ku Eoeun-dong, Taejon, Korea on Jul. 8, 1998, and the number KCTC0500BP was given.

TABLE 1

| Property | SWJ-28 |
|---|---|
| D-Arabinose | − |
| D-Ribose | − |
| D-Xylose | − |
| D-Galactose | − |
| L-Rhamnose | + |
| Maltose | − |
| Sucrose | − |
| Lactose | − |
| Melibiose | − |
| Cellobiose | − |
| Trehalose | + |
| Raffinose | − |
| Melitose | − |
| Methyl-D-Glucoside | − |
| D-Glucosamine | − |
| Inulin | − |
| Methanol | + |
| Ethanol | + |
| Erythritol | − |
| Inositol | − |
| D-Mannitol | + |
| D-Gluconic acid salt | − |
| Glycerin | + |
| Succinic acid | + |
| Citric acid | -or slowly glowing |

TABLE 2

| Property | SWJ-28 |
|---|---|
| Optimum growth pH | pH 6 |
| Optimum growth temperature | 29° C. |
| Nitrate utilization | − |
| Fat decomposition | + |
| Gelatin liquefaction | + |
| Carotinoid production | − |
| Marked production of organic acid | + |
| Production of starch-like materials | − |
| Vitamin requirement | + |
| Malt or YM liquid medium | Medium becomes milky after one day culture at 29° C. Growth is very slow at 37° C. |
| Malt or YM agar medium | Milky colony was formed when cultured at 29° C. for one day. Surface is a little shiny and has minute hypha. |
| Spore production | Sexual sporulation. There is no attachment between Ascomycetes and grow well with matricytes. There are attachment between the cells. One or four hat-shaped spore are formed in the sporangium and detach as the cell grows. |

EXAMPLE 2

Subcloning of Human Lactoferrin Polypeptide

Figure 2:
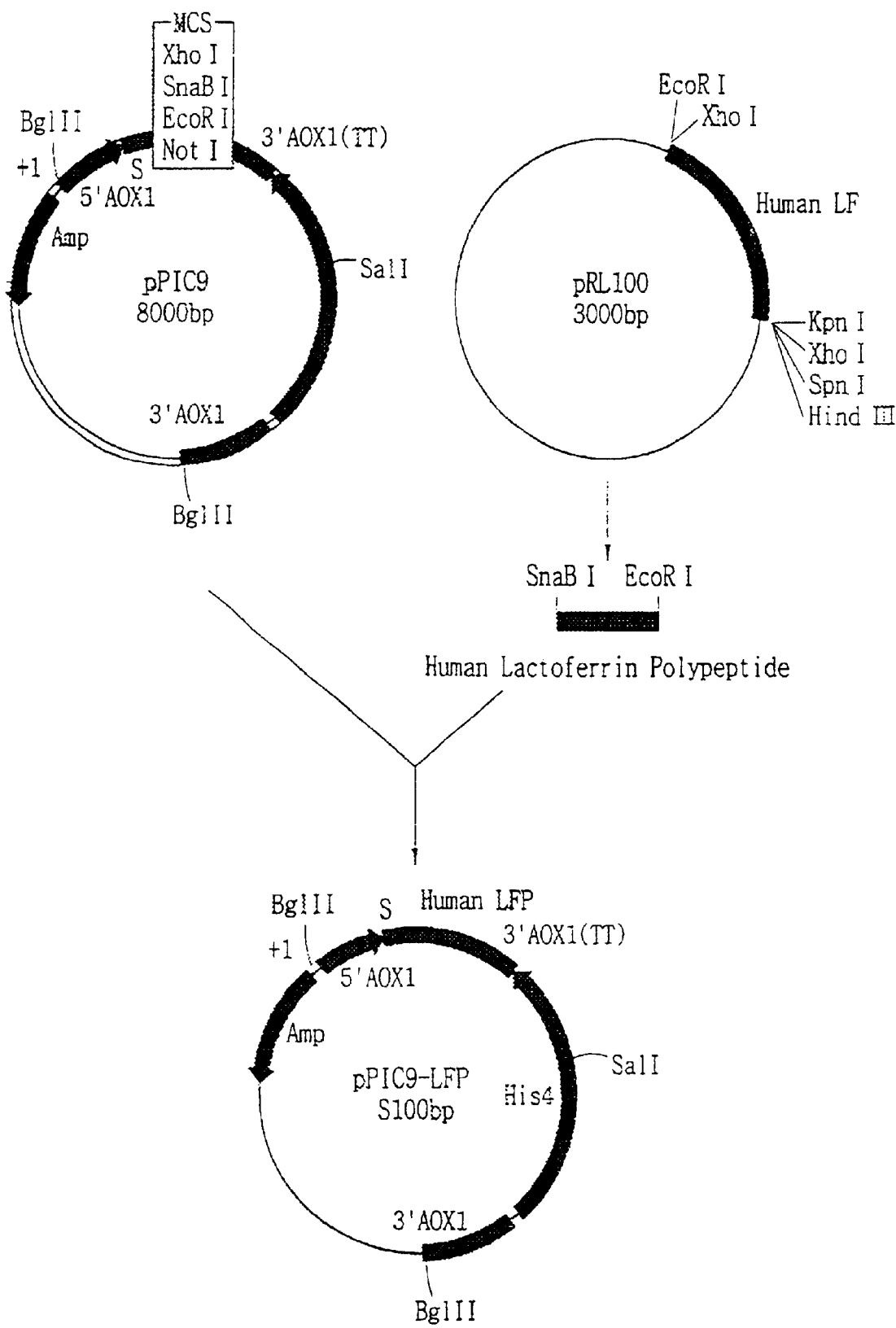
FIG. 2 is a scheme of the preparation method of an expression vector used in the present invention.

The expression vector containing the lactoferrin polypeptide genes was prepared as described in FIG. 2. Primers A (forward; 35mer) and B (backward; 30 mer) identified below were used to obtain a lactoferrin polypeptide gene by performing polymerase chain reaction (PCR) with pRL100 (North Dakota State University, Dept. of Biochemistry, Molecular Biology Laboratory) containing a human lactoferrin gene. The primers A and B were designed to amplify the sequence containing disulfide bond of cysteine in the human lactoferrin base sequence.

Primer A
5'-GGAAGCTTAAAAGATACGTAAAATGCTTC CAATGG-3' (SEQ ID NO: 1)
HindIII SnaBI Primer B
5'-GGGAATTCTCAAAATCTCTTTATGCAGCTG (SEQ ID NO: 2)
EcoRI Lactoferrin polypeptide gene (SEQ ID NO: 3) and amino acid (SEQ ID NO: 4) sequences derived from pRL100
AAATGCTTCCAATGGCAAAGGAATAT-GAGAAAAGTGCGT
KCFQWWRNMRKVR
GGC CCT CCT GTC AGC TGC ATA AAG AGA
GPPVSCIKR Finally amplified lactoferrin polypeptide gene (SEQ ID NO:5) and amino acid (SEQ ID NO:6) sequences
GTAAAATGCTTCCAATGGCAAAG-GAATATGAGAAAAGTGCGTCCT
VKCFQWQRNMRKVRP
Derived from primer A
CCTCCTGTCAGCTGCATAAAGAGATTT
PPVSCIKRF
Derived from Primer B Expression vector pPIC9-LFP was obtained by treating the amplified lactoferrin polypeptide gene and pPIC9 (Invitrogen) with SnaBI and EcoRI and by connecting them. pPIC9-LFP was transformed in *E. coli*, Top 10F'. The transformed colony was selected by obtaining the growing colonies after smearing in an ampicillin containing medium.

EXAMPLE 3

Production of Human Lactoferrin Polypeptide Using SJW-28.

pPIC-LFP was transformed in SJW-28 by electrophoration using the method by Chang etal. (Chang et.al., Guide to electrophoration and electrofusion. Academic Press, p501 (1992)). In other words, after SJW-28 was cultured in YPD liquid medium to $OD_{600}$ 1.3~1.5, pellet was obtained by centrifuging 500 ml of the culture medium. After the pellet was resuspended in 100 ml of YPD, it was treated with 20 mM and 25 mM of HEPES (N-[2-hydroxyethyl]piperazine-N'[2ethanesulfonic acid], pH 8.0) and dithiothreitol, respectively and reacted at 30° C. for 15 minutes. After the solution was dissolved in 0.5 ml of 1M sorbitol, 40 μl was taken and added into a pre-chilled gap cuvette with 100 mg of pPIC9-LFP digested by Sa/l. After the mixture was reacted for 5 minutes in ice, electrophoration was performed at 1500 V and 25 mA. Immediately after the electrophoration, 750 μl of cold 1 M sorbitol was added, and 100 μl of the mixture was smeared in YM medium. Genomic DNA of the transformant that grows in YM medium was purified to finally select the strain in which lactoferrin polypeptide gene had been inserted, by performing PCR using the above mentioned primers A and B.

Figure 3:
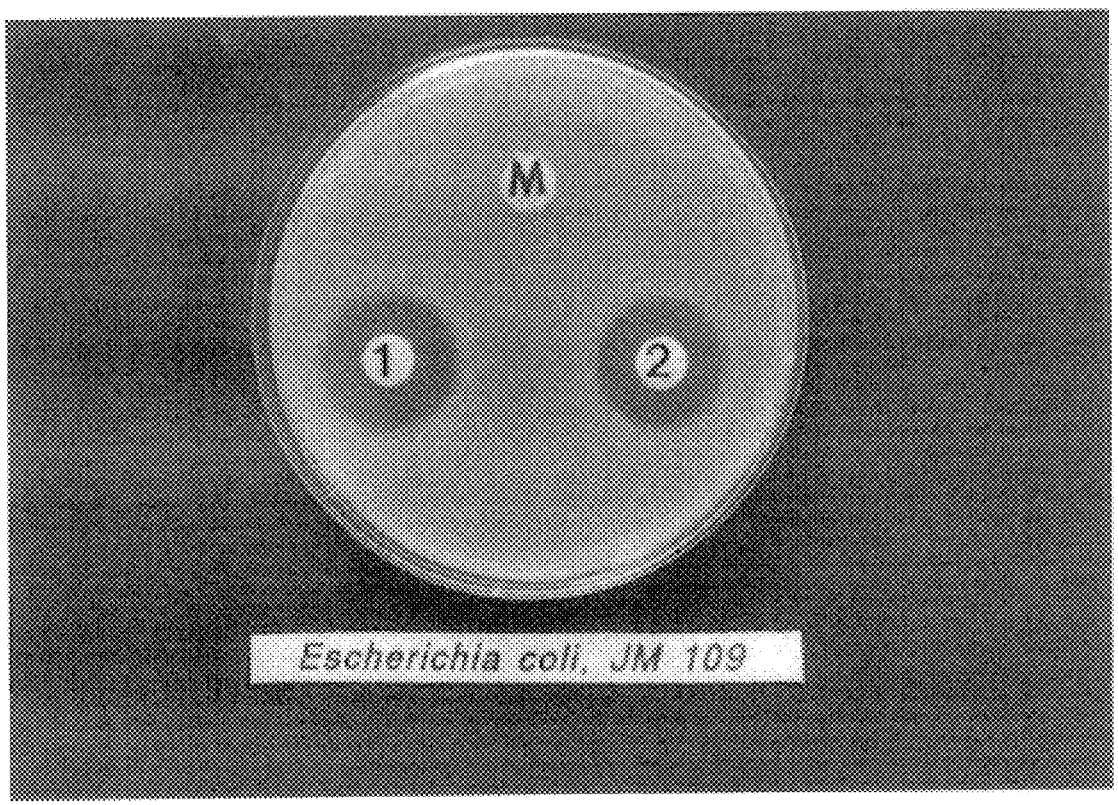
FIG. 3 is a photograph showing the resistance of the transformant by expressing human lactoferrin polypeptide of the present invention against lactoferrin polypeptide.

Lactoferrin polypeptide gene (SEQ ID NO:7) and amino acid (SEQ ID NO:8) sequences produced by the transformant GAGGCTGAAGCTTAAGTAAAATGCTTC-CAATGGCAAAGGAATATG
EAEAYVKCFQWQRNM
Derived from pPIC9, Derived from Primer A
AGAAAAGTGCGTGGCCCTCCTGTCAGCT-GCATAAAGAGATTT
RKVRGPPVSCIKRF
Derived from Primer B After finally selecting the transformant it was cultured to $OD_{600}$ 1.3~1.5 in PD medium, a paper disc that was immersed in the medium containing the transformant was placed on a LB agar medium evenly smeared with *E.coli* JB 109. Antibacterial activity was identified by observing the formation of the clear zone (FIG. 3; M: SJW-28 transformed with pPIC9, 1: transformant, 2: transformant).

EXAMPLE 4

Production of Korean Cow Lactoferrin Polypeptide Using SJW-28.

The following primers were prepared based on the known lactoferrin amino acid sequence.

Forward primer
5'-GGCTCGAGCTTGGACTGTGTCTGGCT-3' (SEQ ID NO: 9)
Xho I

Backward primer
5'-GGCTCGAGTTAATCMAGGGTCACAGCATC (SEQ ID NO:10)
Xho I

A DNA fragment of about 220 bp containing a part of the Korean cow lactoferrin polypeptide was obtained by PCR using the Korean cow lactoferrin cDNA as a template. Expression vector pKLFC was obtained by treating the Korean cow lactoferrin polypeptide gene and pPIC9 (Invitrogen) with XhoI, respectively and by connecting them. pKLFC was transformed in *E coli*, Top 10F'. The transformed colony was selected by obtaining the growing colonies after20 smearing in an ampicillin containing medium. A plasmid containing the Korean cow lactoferrin polypeptide forwardly was selected by the treatment of restriction enzyme and PCR. The plasmid containing the Korean cow lactoferrin polypeptide in forward direction was isolated and this was found to have nearly similar sequence to a part of the cow lactoterrin gene which as reported. The DNA sequences (SEQ ID NO:12) of the Korean cow lactoferrin polypeptide and the DNA sequences (SEQ ID NO:11) of the cow lactoferrin polypeptide were compared as below.

Cow: CTTGGACTGTGTCTGGCTGCCCCGAG-GAAAAACGTTCGATG

Korean Cow: CTTGGACTGTGTCTGGCTGC-CCCGAGGAAAAACGTTCGATG

Cow: GTGTACCATCTCCCMCCCGAGTGGT-TCAAATGCCGCCGCC

Korean Cow: GTGTACCATCTCCCGACCCGAGTG-GTTCAAATGCCGCCGCC

Cow: GATGGCAGTGGAGGATGAA-GAAGCTGGGTGCTCCCTCTATC

Korean Cow: GATGGCAGTGGAGGATGAAG-MGCTGGGTGCTCCCTCTATC

Cow: ACCTGTGTGAGGAGGGCCTTTGCCTG-GMTGTATCCGGGC

Korean Cow: ACCTGTGTGAGGAGGGCCTTTGCCT-TGGAATGTATCCGGGC

Cow: ATCGCGGAGAAAAAGGCGGATGCTGT-GACCCTGGATGGT

Korean cow: ATCGCGGAGMAAAGGCGGATGCTGT-GACCCTTGATTM (stop codon)

As described in Example 3, a plasmid containing the DNA of the Korean cow lactoferrin polypeptide in forward direction was transformed in *Pichia pastoris* SJW-28 by electrophoration. The strain inserted with the lactoferrin polypeptide gene was finally selected with PCR by using the aforementioned forward primer and backward primer.

Figure 4A:
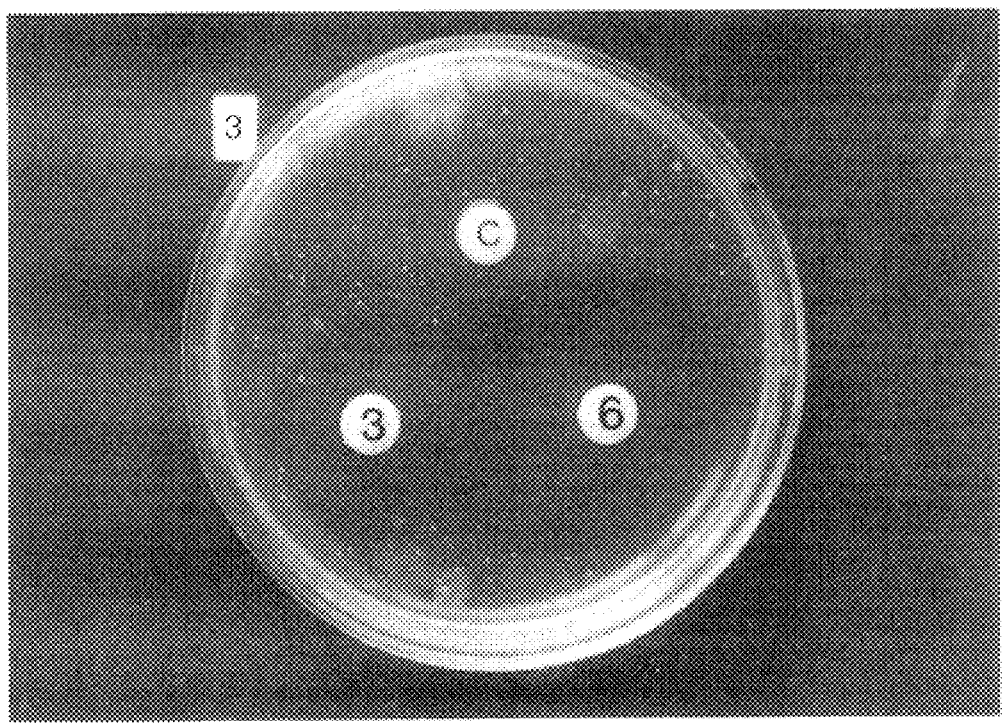
FIGS. 4A~4F are photographs showing the resistance of the transformant by expressing Korean cow lactoferrin polypeptide of the present invention against lactoferrin polypeptide.
Figure 4B:
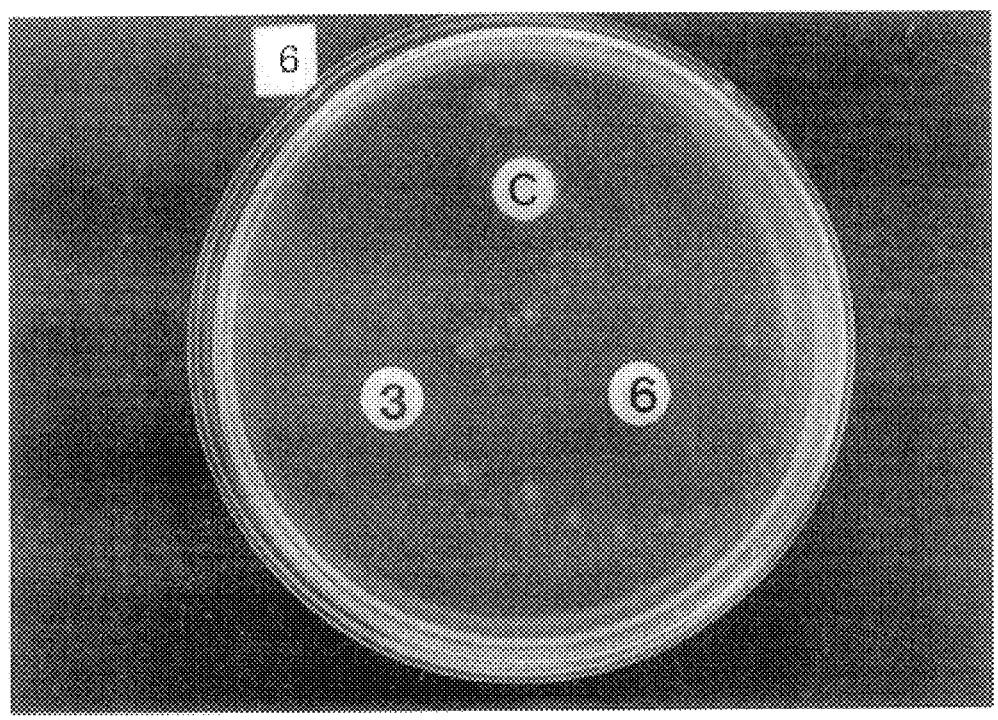
Figure 4C:
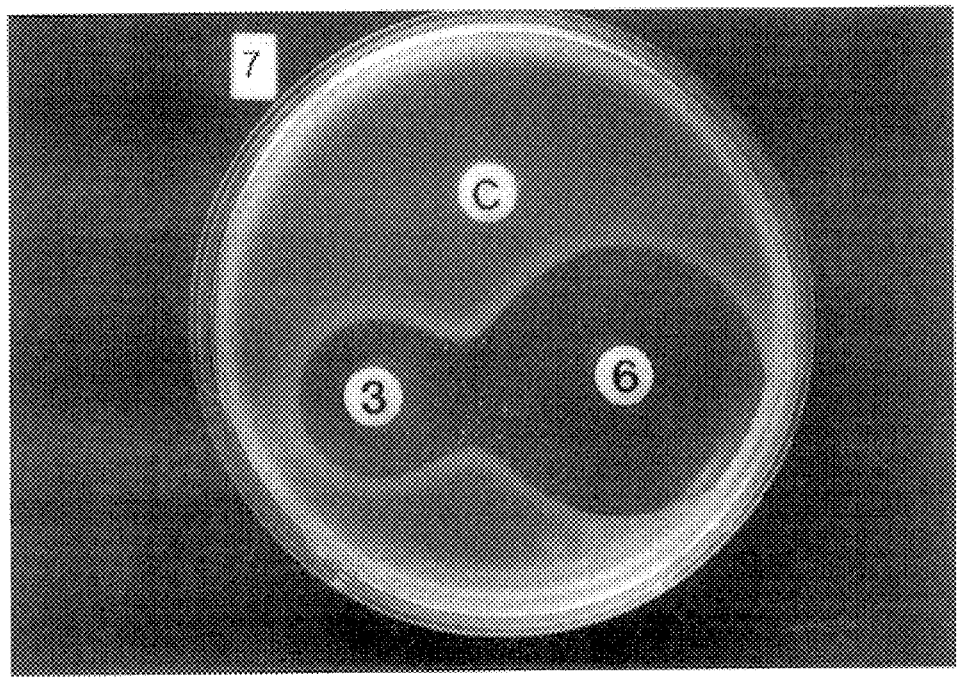
Figure 4D:
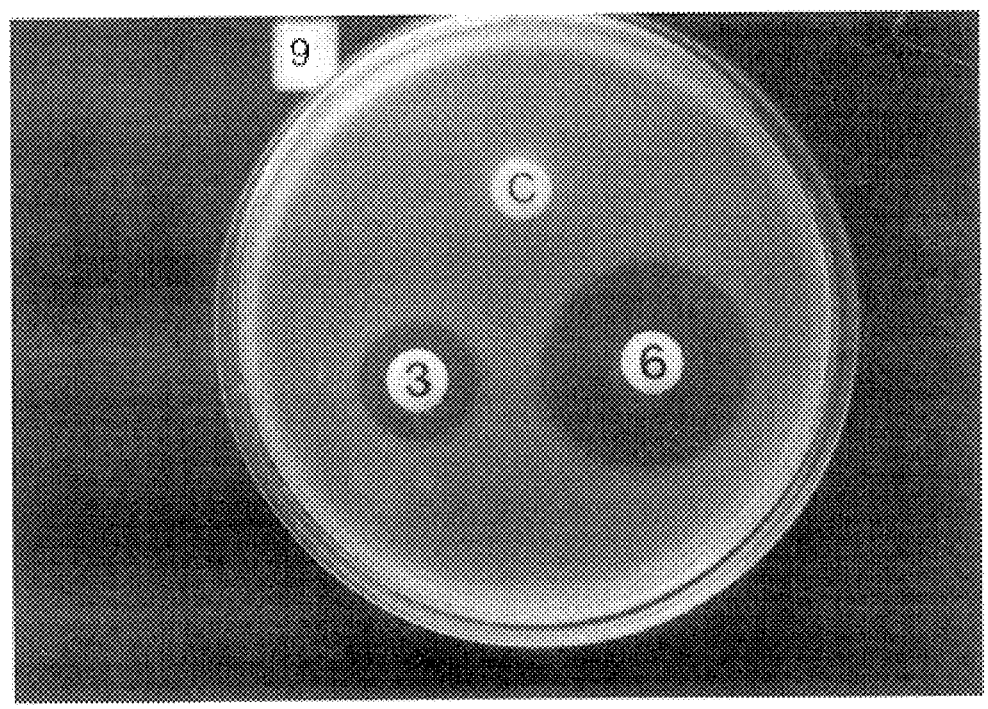
Figure 4E:
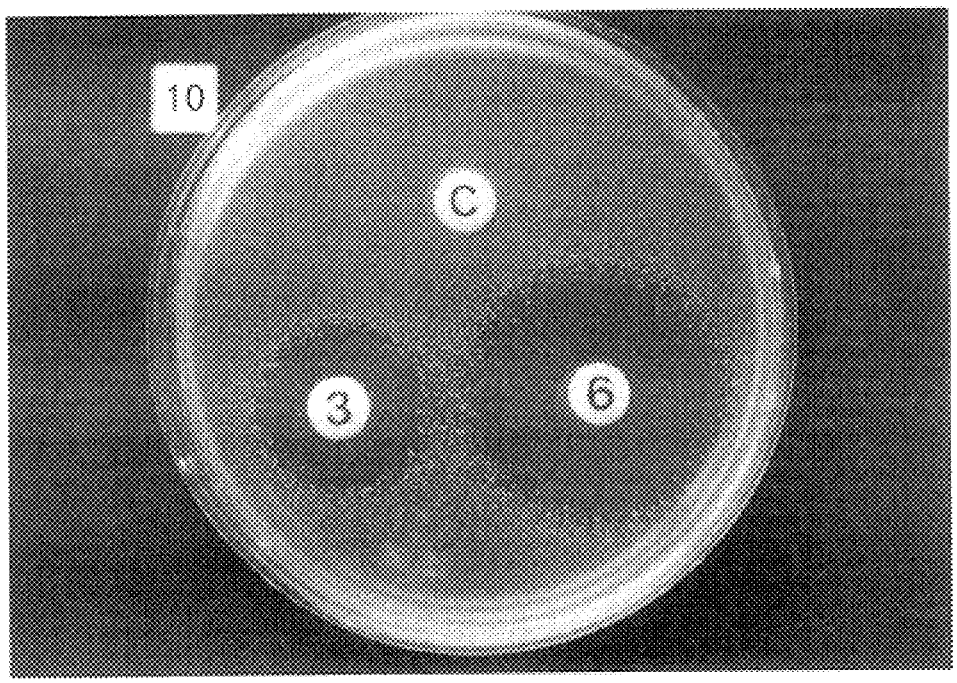
Figure 4F:
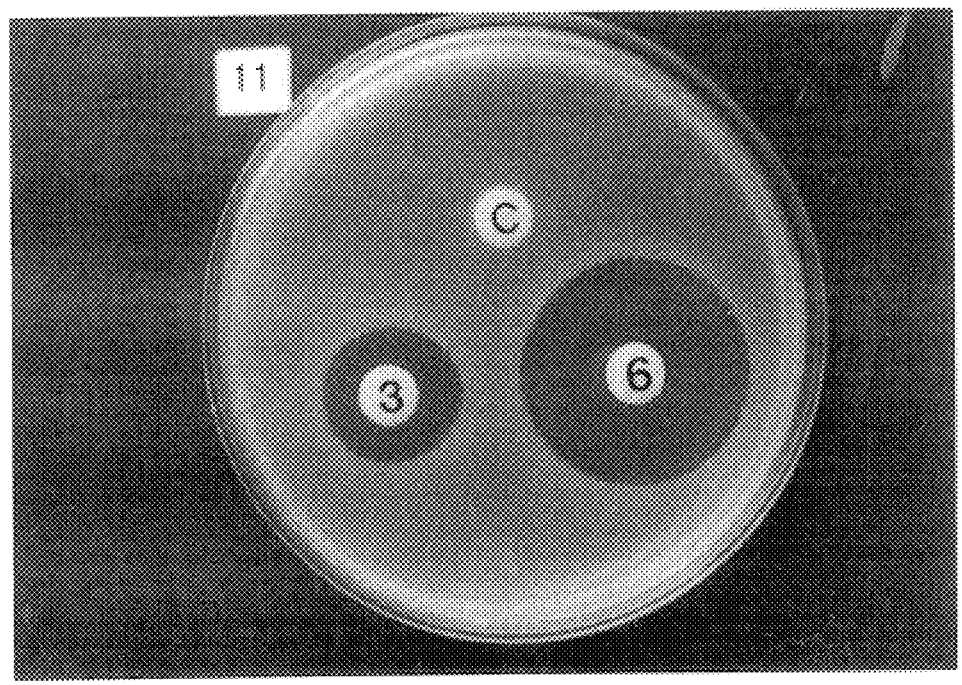

After finally selecting the transformant it was cultured to $OD_{600}$ 1.3~1.5 in YPD medium, a paper disc that was immersed in the medium containing the transformant was placed on a LB agar medium evenly smeared with the test strains. Antibacterial activity was identified by observing the formation of the clear zone. The results were represented in FIGS. 4A~4F wherein the antibacterial activities were tested against the following microorganisms: FIG. 4A: *Streptococcus mutans* KCTC 3065, FIG. 4B: *Psudomonas aerogenosa* KCTC 2004, FIG. 4C: *Enterobacter aerogenos* KCTC 2190, FIG. 4D: *Escherichia coli* JM109 KCTC 2427, FIG. 4E: Salmonella, FIG. 4F: *Escherichia coli* o157:H7. (FIGS. 4A~4F: C: SJW-28; 3: transformant; 6: transformant).

It is possible to mass produce the lactoferrin polypeptide and other antibacterial peptides by the present invention.

What is claimed is:

1. A method of producing a lactoferrin polypeptide having lactoferrin antibacterial activity, which method comprises the following steps:

preparing a plasmid vector comprising a polynucleotide sequence encoding the lactoferrin polypeptide operatively linked to a promoter sequence active in yeast, transforming a *Pichia pastoris* KCTC 0500BP cell with said vector, culturing the transformed cell, and recovering the lactoferrin polypeptide.

2. *Pichia pastoris* KCTC 0500BP.

* * * * *

UNITED STATES PATENT AND TRADEMARK OFFICE
CERTIFICATE OF CORRECTION

PATENT NO. : 6,423,509 B1
DATED : July 23, 2002
INVENTOR(S) : Chang K. Sung et al.

It is certified that error appears in the above-identified patent and that said Letters Patent is hereby corrected as shown below:

<u>Title page,</u>
Item [73], in the residence of the Assignee, "Seaoul" should be -- Seoul --

Item [86], PCT No.: "PCT/KR98/00373" should be -- PCT/KR99/00373 --

Signed and Sealed this

Twenty-second Day of July, 2003

*JAMES E. ROGAN*
*Director of the United States Patent and Trademark Office*